United States Patent
Wang et al.

(10) Patent No.: US 9,476,993 B2
(45) Date of Patent: Oct. 25, 2016

(54) APPARATUS AND METHOD FOR COMPUTING DETECTOR RESPONSE OF A PHOTON-COUNTING DETECTOR

(71) Applicant: Toshiba Medical Systems Corporation, Otawara-shi (JP)

(72) Inventors: Xiaolan Wang, Buffalo Grove, IL (US); Chunguang Cao, Buffalo Grove, IL (US); Yu Zou, Naperville, IL (US)

(73) Assignee: TOSHIBA MEDICAL SYSTEMS CORPORATION, Otawara-shi (JP)

(*) Notice: Subject to any disclaimer, the term of this patent is extended or adjusted under 35 U.S.C. 154(b) by 51 days.

(21) Appl. No.: 14/591,790

(22) Filed: Jan. 7, 2015

(65) Prior Publication Data
US 2016/0195623 A1    Jul. 7, 2016

(51) Int. Cl.
G01T 1/24    (2006.01)
G01N 23/04    (2006.01)

(52) U.S. Cl.
CPC .......... *G01T 1/247* (2013.01); *G01N 23/046* (2013.01)

(58) Field of Classification Search
CPC ...................................................... G01T 1/247
See application file for complete search history.

(56) References Cited

U.S. PATENT DOCUMENTS

| | | | |
|---|---|---|---|
| 2013/0251224 A1 | 9/2013 | Zou | |
| 2014/0314211 A1* | 10/2014 | Zou | G01T 1/171 378/207 |
| 2015/0160355 A1* | 6/2015 | Wang | G01N 23/046 378/19 |

FOREIGN PATENT DOCUMENTS

JP    2013-192951 A    9/2013

* cited by examiner

*Primary Examiner* — Casey Bryant
(74) *Attorney, Agent, or Firm* — Oblon, McClelland, Maier & Neustadt, L.L.P

(57) ABSTRACT

A computed tomography (CT) apparatus and a method for determining response of a photon-counting detector of a CT scanner. Based on a count rate of an incident spectrum and a dead time parameter of the photon-counting detector, a highest pileup order that has a contribution towards an output spectrum of the photon-counting detector greater than a threshold corresponding to the pileup order is determined. In computing the overall output spectrum of the photon-counting detector, only the spectra corresponding to pileup orders lower than or equal to the highest pileup order are considered.

16 Claims, 6 Drawing Sheets

APPARATUS AND METHOD FOR COMPUTING DETECTOR RESPONSE OF A PHOTON-COUNTING DETECTOR

FIELD

Embodiments disclosed herein generally relate to pile-up correction for photon-counting detectors in a spectral computed tomography (CT) system. Specifically, the embodiments described herein relate to a CT system and a method thereof for reducing computational time required in computing a response of the photon-counting detector.

BACKGROUND

Radiographic imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-ray from the generator, the details of the geometry and characteristics of the detector, and the capacity of the acquisition system are all elements that affect how the actual reconstruction is performed. In the reconstruction, the map of the linear attenuation coefficient (LAC) of the imaged subjects is obtained from the line integrals of the LAC through an inverse Radon transform. The line integrals can be related to the logarithm of the primary intensity of the X-rays passing through the subject. However, the measured X-ray intensity on the detector may include both scattering photons and primary photons. Thus, the images reconstructed from scattering may contain some scattering artifacts.

Many clinical applications can benefit from spectral CT technology, which can provide improvement in material differentiation and beam hardening correction. Further, semiconductor-based photon-counting detectors are a promising candidate for spectral CT, which is capable of providing better spectral information compared with conventional spectral CT technology (e.g., dual-source, kVp-switching, etc.).

Due to the dead time (~100 ns), which is determined by the type of semiconductor (e.g. CZT or Cd Te), its thickness and readout circuitry, pulse pileup at high X-ray flux (~10$^8$ cps/mm$^2$) can be very severe, and the measured spectral signals can be distorted. The distorted spectral signal can cause artifacts in the reconstruction of images. If the pileup effect can be corrected in the detector model, the image quality can be improved. However, computing the detector's response while accounting for pileup correction results in significant usage of computational resources of the CT system, and moreover makes the process of determining the response of the photon-counting detector time-intensive.

Accordingly, an efficient technique for reducing computational time required in computing a response of the photon-counting detector is desired.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Embodiments described herein are directed to a CT system and a method for reducing computational time required in computing a response of a photon-counting CT detector.

According to one embodiment, there is provided a computed-tomography (CT) apparatus, including a photon-counting detector configured to receive X-rays emitted from an X-ray source and a processing circuit. The processing circuit is configured to: determine, based on a count rate of an incident spectrum and a dead time parameter of the photon-counting detector, a highest pileup order that has a contribution towards an output spectrum of the photon-counting detector that is greater than a threshold corresponding to the pileup order, calculate, using a detector response model and the incident spectrum, at least one component spectra, wherein each calculated component spectra corresponds to a pileup order that is lower than or equal to the determined highest pileup order, and sum the at least one calculated component spectra to generate the output spectrum.

In another embodiment, there is provided a method for determining a response of a photon-counting detector in a CT scanner, the method including: determining, based on a count rate of an incident spectrum and a dead time parameter of the photon-counting detector, a highest pileup order that has a contribution towards an output spectrum of the photon-counting detector that is greater than a threshold corresponding to the pileup order; calculating, using a detector response model and the incident spectrum, at least one component spectra, wherein each calculated component spectra corresponds to a pileup order that is lower than or equal to the determined highest pileup order; and summing the at least one calculated component spectra to generate the output spectrum.

According to another embodiment, there is provided a non-transitory computer-readable medium having stored thereon a program that when executed by a computer, causes the computer to execute a method including: determining, based on a count rate of an incident spectrum and a dead time parameter of a photon-counting detector in a CT scanner, a highest pileup order that has a contribution towards an output spectrum of the photon-counting detector that is greater than a threshold corresponding to the pileup order; calculating, using a detector response model and the incident spectrum at least one component spectra, wherein each calculated component spectra corresponds to a pileup order that is lower than or equal to the determined highest pileup order; and summing the at least one calculated component spectra to generate the output spectrum.

Figure 1:
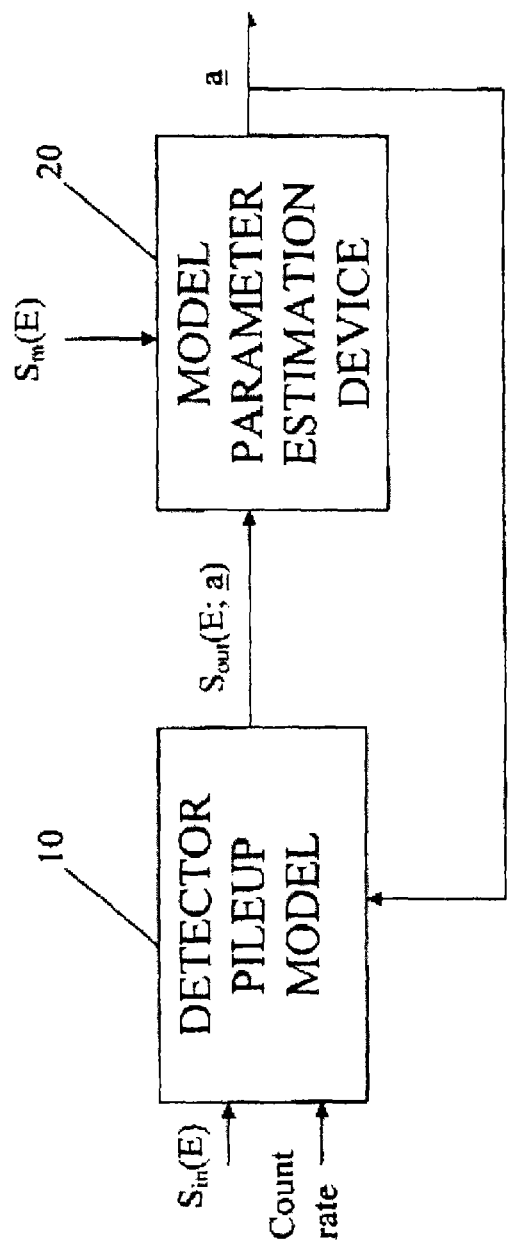
FIG. 1 illustrates an apparatus for determining a detector pileup model for a photon-counting detector.

Turning now to the drawings, FIG. 1 illustrates an apparatus for determining a detector pileup model for each photon-counting detector in a spectral CT scanner. In particular, FIG. 1 illustrates a detector pileup model 10 that receives an incident spectrum $S_{in}(E)$, a count rate, and a parameter vector a. Based on the received values, the detector pileup model 10 generates a simulated measured spectrum $S_{out}(E; a)$. The finally generated spectrum $S_{out}(E; a)$ is used for performing image reconstruction. The process of determining the simulated measured spectrum $S_{out}(E; a)$ will be described in more detail below.

As shown in FIG. 1, the model parameter estimation device 20 compares the simulated measured spectrum $S_{out}(E; a)$ with an actual measured spectrum $S_M(E)$, and updates the parameter vector a so as to minimize a predetermined cost function. The updated parameter vector is fed back to the detector pileup model to generate a new simulated measured spectrum $S_{out}(E; a)$. This process continues for a predetermined number of iterations or until the change in the parameter vector a falls below a predetermined threshold.

The model parameter estimation device can employ, for instance, an exhaustive search within a predefined range for the parameter vector a, or a nonlinear least-squares method for finding the optimal parameter vector a. A respective optimal parameter a is found for each photon-counting detector in a scanner.

The input spectrum $S_{in}(E)$ can be determined by calculation (all vendors have models to calculate the output from their tubes) or measurements (by using a gold-standard spectroscopic detector, e.g., a high-purity germanium spectrometer) for each PCD in a scanner. The measured spectrum $S_M$ is the output spectrum from each PCD corresponding to each incident spectrum.

The parameter vector a includes a dead time value $\tau_d$, a time threshold T to determine whether, e.g., double photon events are peak pileup events or tail pileup events (although this threshold may be applied to determine whether a peak or tail pileup event occurs at any pileup order). Further, the parameter a can also include individual detection probabilities of different number of quasi-coincident photons $\chi_0$, $\chi_1^P$, $\chi_1^t$, $\chi_2^P$, $\chi_2^t$, etc. For example, $\chi_0$ is the detection probability of single photon events, $\chi_1^P$ is the detection probability of peak double pileup events, $\chi_1^t$ is the detection probability of tail double pileup events, $\chi_2^P$ is the detection probability of triple peak pileup events, etc. The sum of individual probabilities will be equal to or less than 1.

Figure 2:
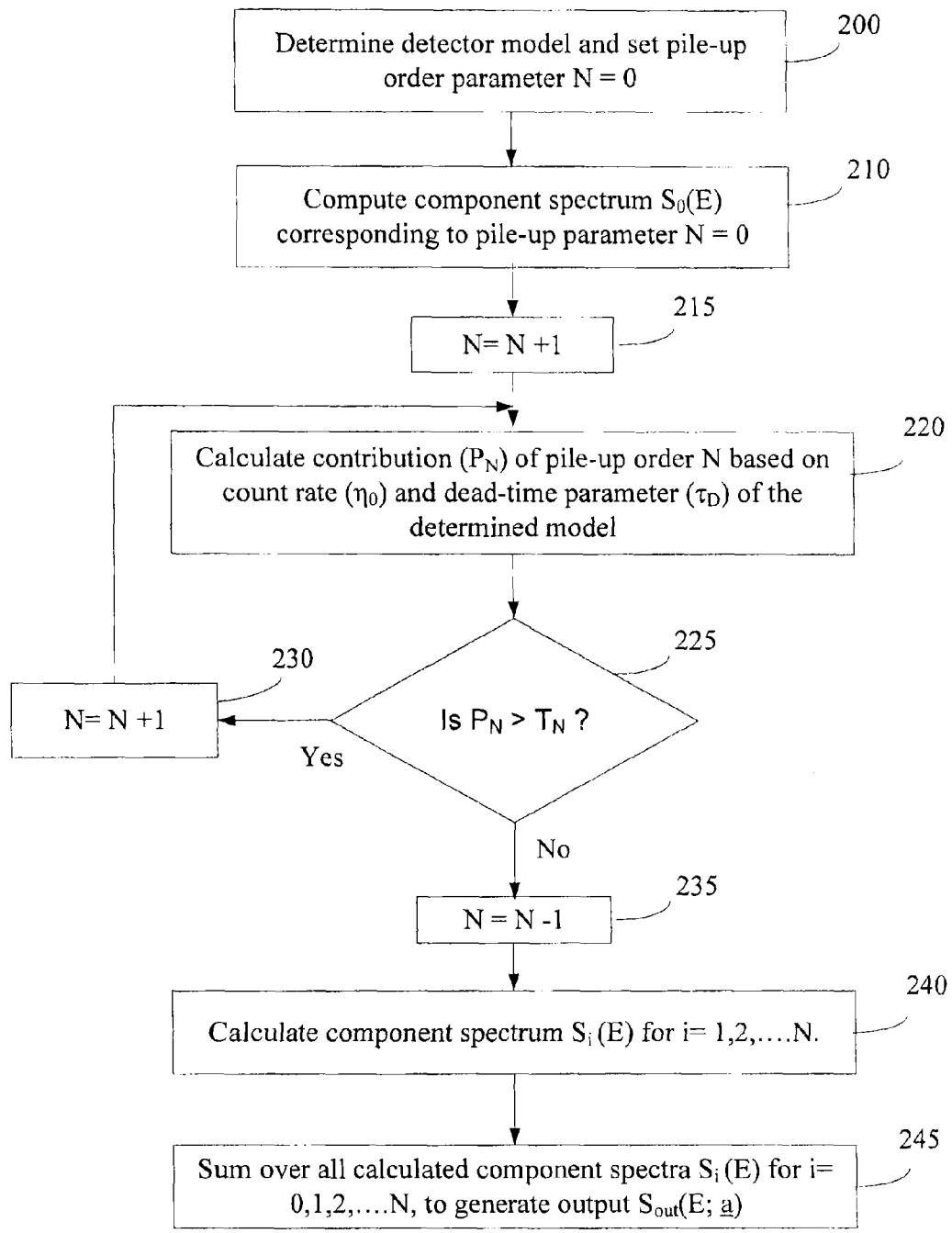
FIG. 2 illustrates a method for determining an output of a detector pileup model for a photon-counting detector.

The detector pileup model 10 computes $S_{out}(E)$ from $S_{in}(E)$ and the parameter a using the method illustrated in FIG. 2.

In particular, in step 200, the parameter vector a that includes the dead time parameter is determined and a pileup order parameter (N) for the photon-counting detector is initialized to zero.

In step 210, a first component spectrum $S_0(E)$ corresponding to the case of N=0 i.e., no pileup is computed based on the input spectrum $S_{in}(E)$ and the parameter vector a.

In step 215, the value of the pile-up order parameter N is incremented by one. In step 220, an upper bound corresponding to the contribution of pileup order N towards the final output spectrum is computed. According to one embodiment, the probability of pileup order N, represented as $P_N$, is a Poisson random variable with a mean value equal to a product of the incident flux $n_0$, (i.e., count rate) and the dead time ($\tau_d$) of the photon-counting detector. Thus, the contribution $P_N$ is computed as:

$$P_N = \frac{(n_0 \times \tau_d)^N}{N!} e^{(-n_0 \times \tau_d)}$$

Further, $P_N$ also serves as an upper bound for the contribution of pileup order N. In the case of peak pileup (i.e., detection probability<1), the actual contribution is smaller than $P_N$, since the number of detected photons is fewer than original number of photons. In the case of tail pileup (i.e., detection probability=1), the actual contribution equals $P_N$ as the photon count is maintained. Thus, as all pileup events are a combination of both cases, the actual contribution cannot be higher than $P_N$. Note that for increasing values of N, the value of $P_N$ decreases. Therefore, once a particular $P_N$ is deemed negligible based on the corresponding threshold, all pile-up orders greater than N can also be considered negligible. Furthermore, the probability of photon pile-up order herein is assumed to have a Poisson distribution. However, the method steps described herein are equally applicable to probabilities of photon pile-up that have other distributions.

In step 225, a query is made to determine if the contribution of the $N^{th}$ order pileup is greater than a predetermined threshold value, $T_N$. For each order N, the threshold value $T_N$ can be determined empirically or may be determined based on a desired level of accuracy in computing the photon-counting detector's response. If the response to the query is affirmative, the process moves to step 230, wherein the value of the pileup parameter is incremented by one and the process loops back to step 210, in order to compute the contribution of the next order of pileup to the final output spectrum.

If the response to the query in step 220 is negative, the process moves to step 235 wherein the value of the pileup parameter is decremented by one. This ensures that the output spectrum Sout(E; a) is computed only for those orders of pileup that satisfy the condition in step 225. Specifically, only the pileup orders whose contribution is greater than the predetermined threshold corresponding to each pileup order are accounted for in the computation of the output spectrum.

The individual component spectra $S_i(E)$ for i=1, 2, 3, . . . N are computed in step 240. According to an embodiment, a Poisson distribution is assumed for the single photon events and the effects of pixel weighting potential, depth of interaction, ballistic deficit, and space charge are included in the calculation of $S_i(E)$. Note that the use of the Poisson distribution is reflected in the terms $$e^{-n\tau_d}, ne^{-n\tau_d}, \frac{1}{2}n^2 e^{-n\tau_d},$$

etc. of the component spectra equations (S0, S1, S2, etc.) shown below.

In particular, the weighting potential is defined as follows:

$$w(z) = \frac{z}{L} - \alpha \sin\frac{\pi z}{L}, 0 \le z \le L$$

$$z = \begin{cases} z_0, t < 0 \\ v_e t + z_0, 0 \le t \le t_{TOF} \\ L, t > t_{TOF} \end{cases} = \frac{L - z_0}{v_e}$$

where z indicates the distance between a point in CZT and the cathode, $z_0$ is the point where an X-ray photon converts to electron-hole pairs, $t_{TOF}$ is the time for the generated electrons to drift from the interaction point $z_0$ to the anode of the detector. Also, $\alpha$ is a model parameter describing the weighting potential distribution of the detector, L is the detector thickness, and $\upsilon_e$ is the drifting velocity of the electron carriers in the photon-counting detector.

For ballistic deficit, the basic equations are:

$$\tau_p \frac{dv_p(t)}{dt} + v_p(t) = \tau_p \frac{dv_{in}(t)}{dt}$$

$$v_{in}(t) = KE[w(z(t)) - w(z_0)]$$

where E is the incident energy, and K is the front-end gain (a constant for a given readout configuration), $\tau_p$ is the time constant of the pre-amplifier, and $\upsilon_p(t)$ is the output voltage of the pre-amplifier.

For $0 \le t \le t_{TOF}$, from the basic equations, the pre-amplifier output can be written as:

$$v_p(t) = e^{-\frac{t}{\tau_p}} \left[ \int dt KE \frac{dz(t)}{dt} \frac{dw(z)}{dz} e^{\frac{t}{\tau_p}} + v^0 \right]$$

where $\upsilon^0$ is determined by the initial condition, $$\upsilon_p(0)=0.$$

Inserting the weighting potential equations into above equation, we have, $$v_p(t) = e^{-\frac{t}{\tau_p}} \left[ \int dt KE v_e \left( \frac{1}{L} - \alpha \frac{\pi}{L} \cos \frac{\pi(v_e t + z_0)}{L} \right) e^{\frac{t}{\tau_p}} + v^0 \right].$$

Calculating the integration, we have $$v_p(t) =$$
$$e^{-\frac{t}{\tau_p}} \left[ KEv_e \left( \frac{\tau_p}{L} - \alpha \frac{\pi}{L} \frac{\frac{1}{\tau_p} \cos \frac{\pi(v_e t + z_0)}{L} + \frac{\pi v_e}{L} \sin \frac{\pi(v_e t + z_0)}{L}}{\left(\frac{\pi v_e}{L}\right)^2 + \left(\frac{1}{\tau_p}\right)^2} \right) e^{\frac{t}{\tau_p}} + v^0 \right].$$

Applying the initial condition, the constant $\upsilon^0$ can be expressed as, $$v^0 = -\frac{KE\tau_p}{\tau_{TOF}} \left( 1 - \frac{\alpha\pi \left( \cos \frac{\pi z_0}{L} + \frac{\pi \tau_p}{\tau_{TOF}} \sin \frac{\pi z_0}{L} \right)}{\left(\frac{\pi \tau_p}{\tau_{TOF}}\right)^2 + 1} \right), \text{ where}$$

$$\tau_{TOF} = \frac{L}{v_e}. \text{ At}$$

$$t_{TOF} = \frac{L - z_0}{v_e},$$

the generated electron will reach the anode of the detector. Accordingly, the pre-amplifier output reaches the maximum, $$v_p(t_{TOF}) = \frac{KE\tau_p}{\tau_{TOF}} \left( 1 - \frac{\alpha\pi}{\left(\frac{\pi \tau_p}{\tau_{TOF}}\right)^2 + 1} \right) + v^0 e^{-\frac{t_{TOF}}{\tau_p}}.$$

Note that $t_{TOF}$ will be different if space charge becomes non-negligible.

For the case $t > t_{TOF}$, after $t_{TOF}$, the signal collection is complete and the output amplitude decays exponentially with the front-end circuitry time constant, $\tau_p$.

$$v_p(t) = v_p(t_{TOF})e^{-\frac{t-t_{TOF}}{\tau_p}}$$

As illustrated above, the formulation of $\tau_p(t)$ depends on depth of interaction, $z_0$ and the incident energy, $E_0$. Therefore, we will denote it as $\tau_p(t)=\tau_p(t; z_0, E_0)$. Below, for ease of representation, we may omit $E_0$ in $\tau_p(t)$. Below, we also use $\{t_{TOF}^j; z_j\}$ to define the time-of flight and depth-of-interaction of photon j, respectively.

For the no pileup case, the first component spectrum is calculated as follows. First, the detected energy, E, is defined as $$E = v_p(t_{TOF}^0; z_0, E_0).$$

Next, the component spectrum becomes:

$$S_0(E) = e^{-n\tau_d} \iint dz_0 dE_0 \chi_0 S_{in}(E_0) e^{-\mu_{CZT}(E_0)z_0} \mu_{CZT}(E_0)$$

where the integration runs over the whole volume with the energy condition. Note that detection probability $\chi_0 \sim 1$ if the flexible dead time close to true dead time. In the above equation, n is the incident count rate and $\mu_{CZT}(E)$ is the linear attenuation of CZT at energy E.

According to one embodiment, a second component spectrum $S_1(E)$ for double photon events including peak pileup events and tail pileup events is calculated using $S_{in}(E)$ and the parameter vector a. For double photon events, a peak pileup event is determined to have occurred when the time interval between events is smaller than a threshold T, and a tail pileup event is determined to have occurred when the time interval is larger than the threshold T. The threshold T is included in the model parameter vector a.

In particular, for peak pileup events, the energy is defined as:

$$E = v_p(t_{TOF}^0; z_0)e^{-\frac{t_{max}-t_{TOF}^0}{\tau_p}} + v_p(t_{TOF}^1; z_1)e^{-\frac{t_{max}-t_{TOF}^1-t_1}{\tau_p}}$$

$$t_{max} = \max(t_1 + t_{TOF}^1, t_{TOF}^0)$$

Then the peak component spectrum becomes:

$$S_1^P(E) = ne^{-n\tau_d} \iiiiint dz_0 dE_0 dt_1 dz_1 dE_1 \chi_1^P S_{in}(E_0) S_{in}(E_1) e^{-\mu_{CZT}(E_0)z_0 - \mu_{CZT}(E_1)z_1} \mu_{CZT}(E_0) \mu_{CZT}(E_1)$$

Note that detection probability $$\chi_1^P \sim \frac{1}{2},$$

it the flexible dead time close to the true dead time.

For tail pileup, the first peak energy is defined as:

$$E^0 = v_p(t_{TOF}^0; z_0) + v_p(t_{TOF}^0 - t_1; z_1)$$

Then, the component spectrum becomes:

$$S_1^{t0}(E) = ne^{-n\tau_d} \iiiiint dz_0 dE_0 dt_1 dz_1 dE_1 \chi_1^{t0} S_{in}(E_0) S_{in}(E_1) e^{-\mu_{CZT}(E_0)z_0 - \mu_{CZT}(E_1)z_1} \mu_{CZT}(E_0) \mu_{CZT}(E_1)$$

Further, the second peak energy is defined as:

$$E^1 = v_p(t_{TOF}^1 + t_1; z_0) + \tau_p(t_{TOF}^1; z_1)$$

Then the component spectrum becomes:

$$S_1^{t1}(E) = ne^{-n\tau_d} \iiiii dz_0 dE_0 dt_1 dz_1 dE_1 \chi_1^{t1} S_{in}(E_0) S_{in}(E_1) e^{-\mu_{CZT}(E_0)z_0 - \mu_{CZT}(E_1)z_1} \mu_{CZT}(E_0) \mu_{CZT}(E_1)$$

Note that detection probability $\chi_1^{t0} \sim 0$, $\chi_1^{t1} \sim 0$ if the flexible dead time is close to the true dead time. The peak and tail pileup component spectrum are added to form $S_1(E)$.

Further, multiple photon events including peak pileup events and tail pileup events is calculated using $S_{in}(E)$ and the parameter vector a. In particular, in the triple pileup case, for peak pileup, the energy is defined as:

$$E = v_p(t_{TOF}^0; z_0) e^{-\frac{t_{max} - t_{TOF}^0}{\tau_p}} +$$
$$v_p(t_{TOF}^1; z_1) e^{-\frac{t_{max} - t_{TOF}^1 - t_1}{\tau_p}} + v_p(t_{TOF}^2; z_2) e^{-\frac{t_{max} - t_{TOF}^2 - t_2}{\tau_p}}$$

$$t_{max} = \max(t_2 + t_{TOF}^2, t_1 + t_{TOF}^1, t_{TOF}^0)$$

Then, the peak component spectrum becomes:

$$S_2^p(E) =$$
$$\frac{1}{2} n^2 e^{-n\tau_d} \int\int\int\int\int\int\int\int\int dz_0 dE_0 dt_1 dz_1 dE_1 dt_2 dz_2 dE_2 \chi_2^p S_{in}(E_0)$$
$$S_{in}(E_1) S_{in}(E_2) \times$$
$$e^{-\mu_{CZT}(E_0)z_0 - \mu_{CZT}(E_1)z_1 - \mu_{CZT}(E_2)z_2} \mu_{CZT}(E_0)\mu_{CZT}(E_1)\mu_{CZT}(E_2)$$

Note that detection probability $$\chi_2^p \sim \frac{1}{3}$$

if the flexible dead time close to the true dead time. As an approximation:

$$S_2^p(E) \approx$$
$$\frac{1}{2} n^2 e^{-n\tau_d} \int\int\int dE' dz_2 dE_2 \chi_2^p S_{norm}(E') S_{in}(E_2) e^{-\mu_{CZT}(E_2)z_2} \mu_{CZT}(E_2)$$

where, $S_{norm}(E) = N[S_0(E) + S_1^p(E) + S_1^{t0}(E) + S_1^{t1}(E)]$, where N is a normalization factor.

For the tail pileup case or the mixed tail-peak pileup case, the calculation is similar to that of double pileup, but there are more combinations to consider. For example, for a first combination (0-1-2), the energy is defined as:

$$E^0 = v_p(t_{TOF}^0; z_0) + v_p(t_{TOF}^0 - t_1; z_1) + v_p(t_{TOF}^0 - t_2; z_2)$$

$$E^1 = v_p(t_{TOF}^1 + t_1; z_0) + v_p(t_{TOF}^1; z_1) + v_p(t_{TOF}^1 + t_1 - t_2; z_2)$$

$$E^2 = v_p(t_{TOF}^2 + t_2; z_0) + v_p(t_{TOF}^2 + t_2 - t_1; z_1) + v_p(t_{TOF}^2; z_2)$$

For a second combination ((01)-2), the energy is defined as:

$$E^{01} = v_p(t_{max}; z_0) + v_p(t_{max} - t_1; z_1) + v_p(t_{max} - t_2; z_2)$$

$$t_{max} = \max(t_1 + t_{TOF}^1, t_{TOF}^0)$$

$$E^2 = v_p(t_{TOF}^2 + t_2; z_0) + v_p(t_{TOF}^2 + t_2 - t_1; z_1) + v_p(t_{TOF}^2; z_2)$$

Figure 3:
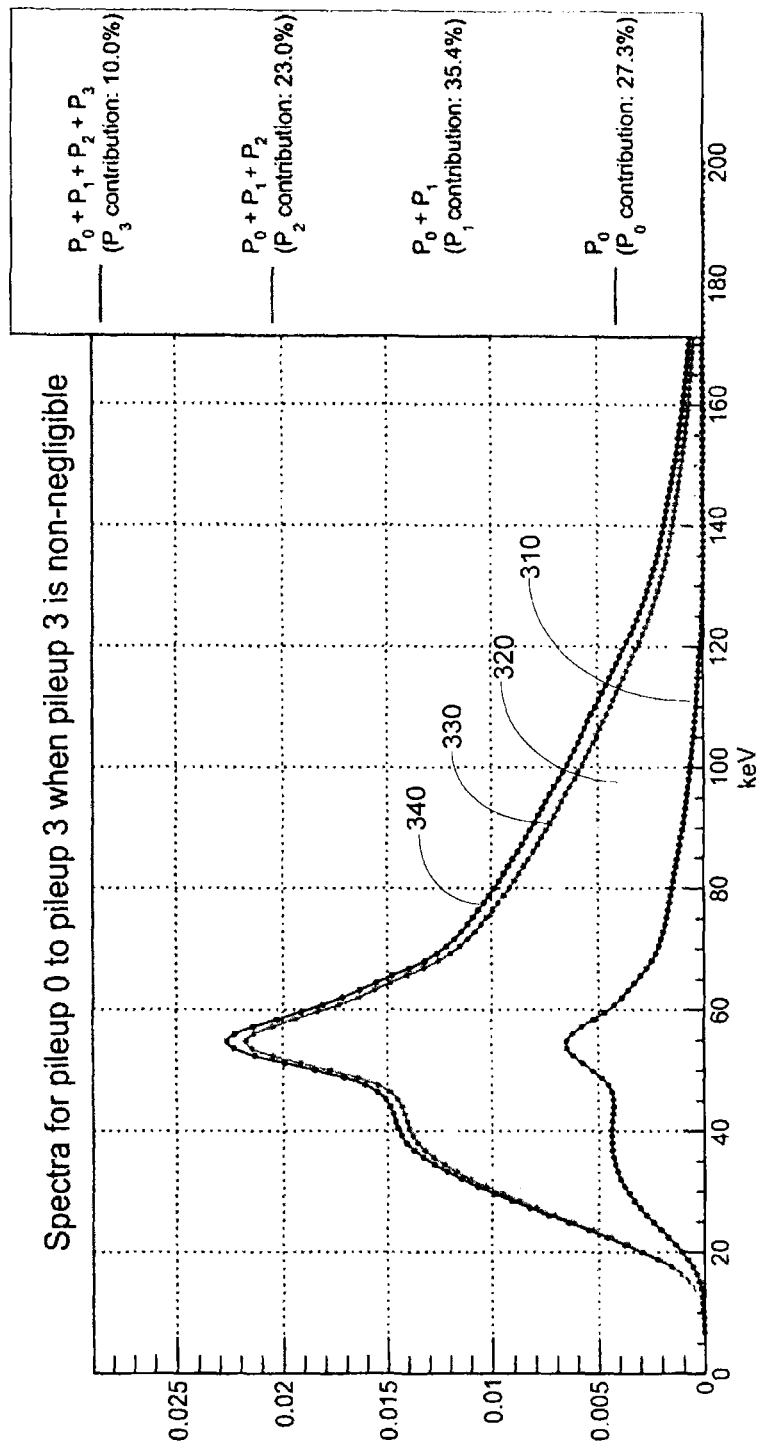
FIGS. 3 and 4 illustrate simulated component spectra using a detector pileup model.
Figure 4:
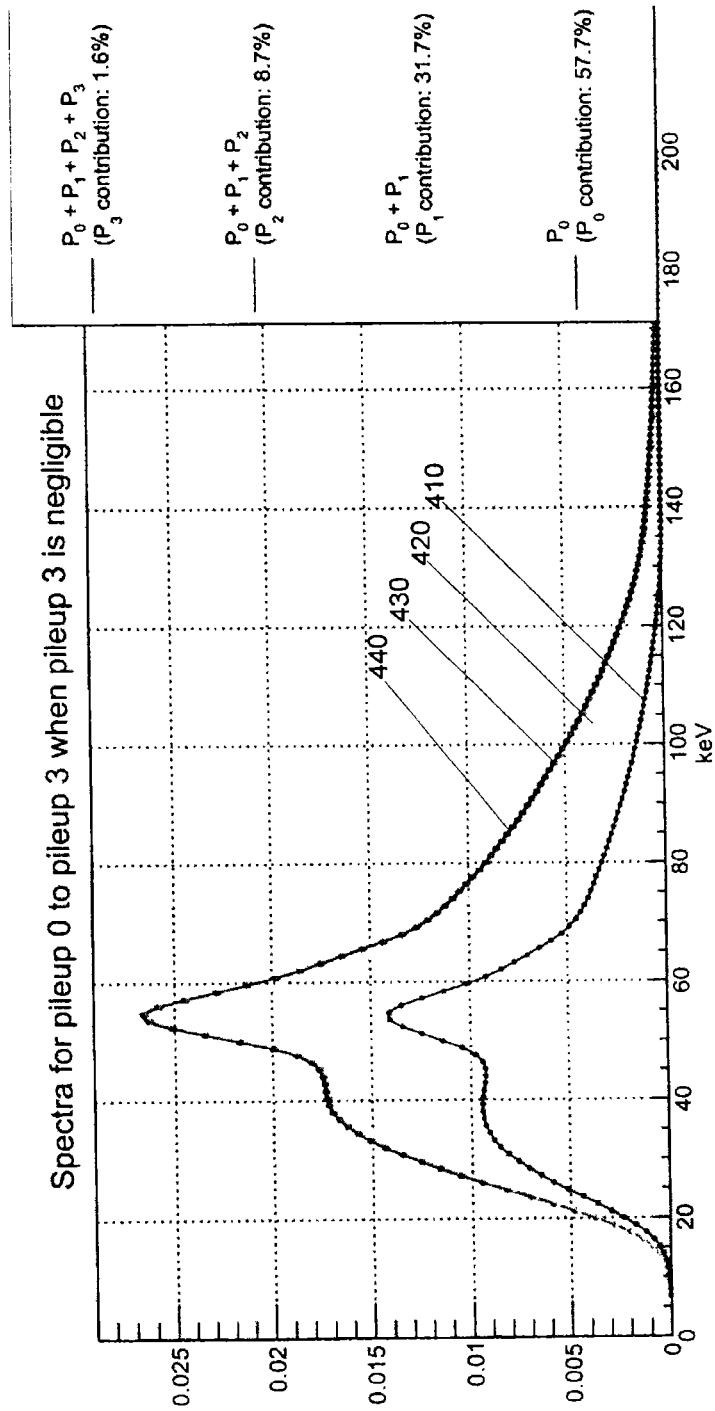

Other combinations, such as ((02)-1) and ((12)-0) are similar to the second combination set forth above. Furthermore, the above described approach can be extended to higher-order pileup events. Note that in step 240, the component spectra are computed only for those pileup events that satisfy the criteria in step 225. FIGS. 3 and 4 describe an example illustrating the computation of different pileup orders of a photon-counting detector.

Upon computing the component spectra in step 240 the process moves to step 245, wherein the calculated component spectra $S_i(E)$, $i=0, 1, 2 \ldots N$, are summed to generate the output spectrum $S_{out}(E; a)$. Note that the pileup order N need only be calculated once through steps 200-235 shown in FIG. 2, and is then used in steps 240 and 245 to calculate and sum the component spectra.

FIGS. 3 and 4 depict simulated component spectra according to one embodiment. For sake of convenience, the spectra depicted in FIGS. 3 and 4 include contributions from pileup order N=0 to pileup order N=3.

In FIG. 3, curve 310 corresponds to the contribution for the case of having no pileup (i.e., N=0). The contribution from $P_0$ towards the final output spectrum is 27.3%. The curve 320 corresponds to the case where the output spectrum includes contributions from $P_0$ (N=0, no pile up) and $P_1$ (N=1, first order pileup). The contribution towards the output spectrum from P1 is 35.4%. Similarly curves 330 and 340 represent the scenarios that include spectrum contributions from $P_0$, $P_1$, and $P_2$ and $P_0$, $P_1$, $P_2$ and $P_3$, respectively.

In the present embodiment, the respective thresholds for pileup order N=0 to pileup order N=3 are $T_0=1\%$, $T_1=1\%$, $T_2=1.5\%$, and $T_3=2\%$. Note, that since the contribution of pileup order $P_3$ is 10%, the contribution is greater than the threshold $T_3=2\%$, and is thus considered in computing the output spectrum of the photon-counting detector.

In contrast, FIG. 4 depicts the curves 410-440 that correspond to the contributions of pileup order N=0 to pileup order N=3. In this case, the contribution from P3 is equal to 1.6%. Since the contribution from the pileup order N=3 is less than the threshold of $T_3=2\%$, the contribution is determined to be negligible and is thus not considered in computing the output spectrum of the photon-counting detector. The contribution from pile up order N=3 is insignificant, as is evident from the fact that curve 440 almost overlaps curve 430. Thus, in computing the output spectrum of the photon-counting detector, only the contributions from pile up orders N=0, 1, and 2 are considered. In other words, the contributions from pileup orders N=3, 4, 5 etc. are ignored in the computation of the output spectrum. Thus, the user-defined thresholds ($T_N$) that may be based on the desired level of accuracy, dictate the pileup orders ($P_N$) that are considered in the computation of the output spectrum. Accordingly, by restricting the number of pileup orders in the computation of the output spectrum, a reduction in the computational time required to compute the response of a photon-counting detector is achieved.

Figure 5:
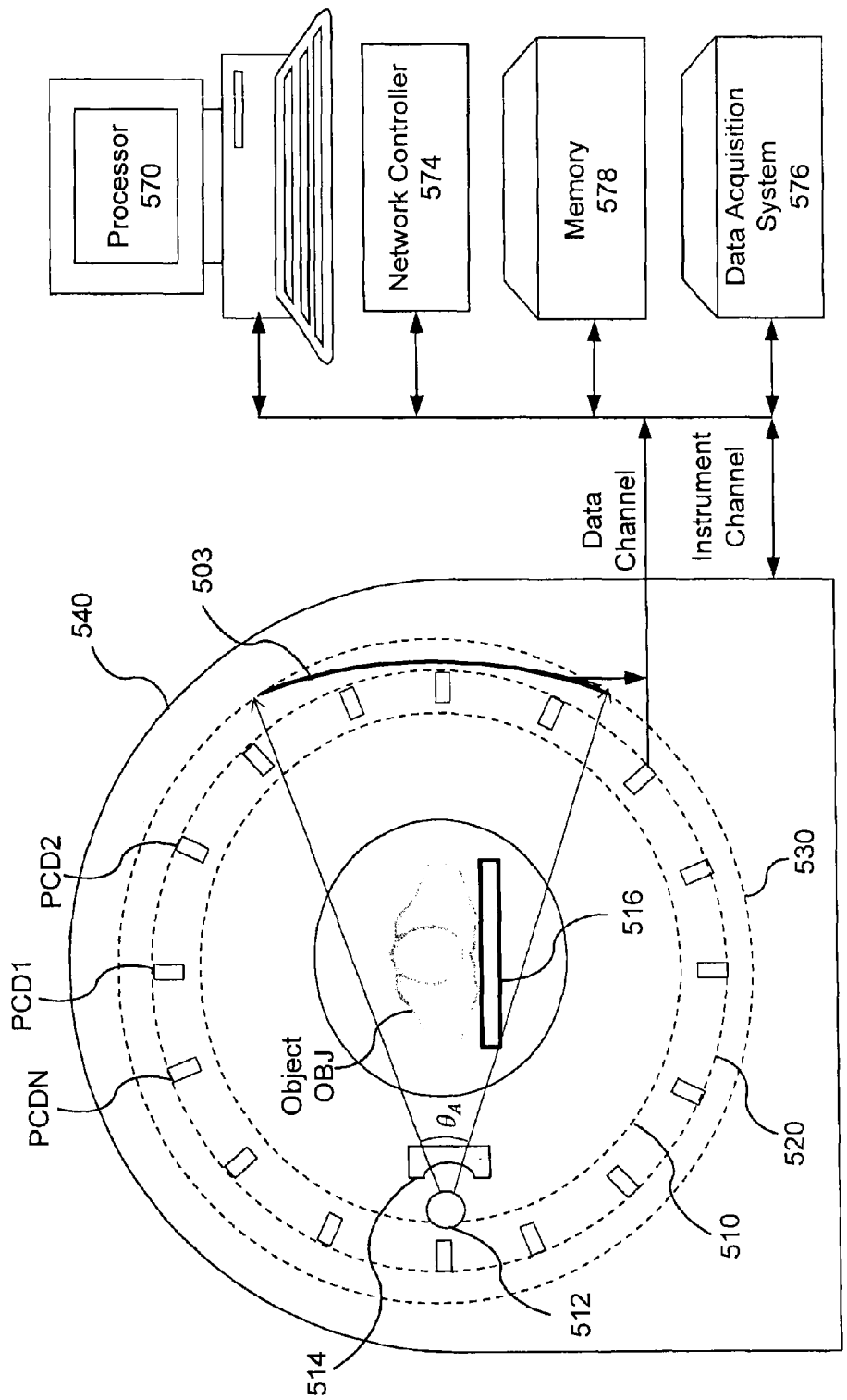
FIG. 5 shows a schematic diagram of an implementation of an image reconstruction apparatus having a coupled-ring topology.
Figure 6:
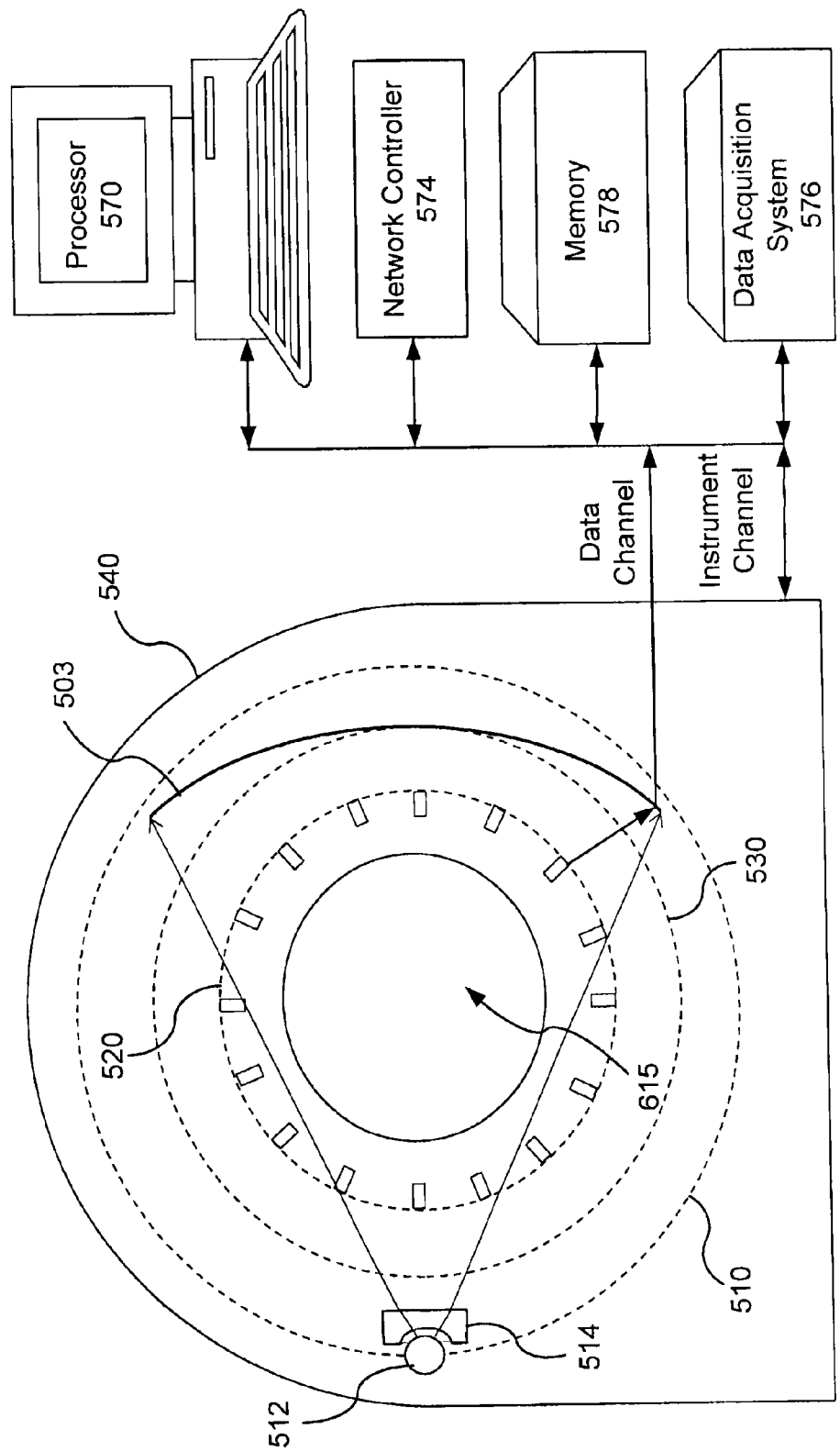
FIG. 6 shows a schematic diagram of an implementation of an image reconstruction apparatus having an inner-ring topology.

FIG. 5 and FIG. 6 show schematic views of CT scanner systems with hybrid systems having energy-integrating detectors arranged in a third-generation geometry and photon-counting detectors (PCDs) arranged in a fourth-generation geometry. FIG. 5 shows a coupled-ring topology with the X-ray source 512 inside the ring of PCDs and the X-ray detector unit 503 outside the ring of PCDs, as discussed in U.S. patent application Ser. No. 13/426,903, incorporated herein by reference in its entirety. In contrast, FIG. 6 shows an inner-ring topology with both the X-ray source 512 and the X-ray detector unit 503 outside the ring of PCDs, as discussed in U.S. patent application Ser. No. 14/092,998, incorporated herein by reference in its entirety. Embodiments disclosed herein can also be implemented for CT scanners having a third-generation geometry in which the detectors are PCDs.

Illustrated in FIG. 5 is an implementation for placing the PCDs in a predetermined fourth-generation geometry in combination with a detector unit 503 in a predetermined third-generation geometry in a CT scanner system. The diagram illustrates relative positions among an object OBJ to be scanned resting on a table 516, an X-ray source 512, a collimator/filter 514, an X-ray detector 503, and photon-counting detectors PCD1 through PCDN. The PCDs have a front surface, oriented towards the object OBJ and a back surface oriented away from the object OBJ. X-rays traveling through the object OBJ are either detected by the PCDs (at the front surface) or pass through the spaces between the sparsely arranged PCDs and are detected by the tightly packed energy-integrating detectors in the X-ray detector 503.

Also shown in FIG. 5 is circuitry and hardware for acquiring, storing, processing, and distributing X-ray projection data. The circuitry and hardware include: a processor 570, a network controller 574, a memory 578, and a data acquisition system 576. In one implementation, the X-ray source 512 and the collimator/filter 514 are fixedly connected to a first rotational component 510 that is rotatably connected to a gantry 540. The X-ray detector 503 is similarly fixedly connected to a second rotational component 530 that is rotatably connected to the gantry 540. While, the PCDs are fixedly connected to a circular component 520 that is fixedly connected to the gantry 540. The gantry 540 houses many pieces of the CT scanner.

The gantry of the CT scanner also includes an open aperture 615 (shown in FIG. 6) enabling the object OBJ that is arranged on a table 516 positioned in a projection plane of the X-rays traveling from the X-ray source to the PCDs and detector unit 503. The "projection plane" is a volume wherein X-rays pass from the X-ray source 512 to the detectors including the PCDs and the detector unit 503. The "object space" is the intersection of the projection plane and the open aperture 615 of the gantry. The "image space" includes the union of projection planes corresponding to all projection angles of the X-ray source 512, as the X-ray source rotates around the aperture of the gantry. The image space is generally larger than the object space enabling image reconstruction for a volume that may be greater than the object.

A scan is performed when an object OBJ occupies the object space and the X-ray source is rotated through a series of projection angles with the CT scanner acquiring projection data of the X-ray transmission/attenuation through the object OBJ at each projection angle.

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 5 includes a detector unit 503 having energy-integrating detectors arranged in a conventional third-generation geometry. The detector elements in the detector unit 503 can be more densely placed along the detector unit surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined third circular component 520 in a gantry. In one implementation, the photon-counting detectors PCD1 through PCDN are fixedly placed on the circular component 520 at predetermined equidistant positions. In an alternative implementation, the photon-counting detectors PCD1 through PCDN are fixedly placed on the circular component 520 at predetermined non-equidistant positions. The circular component 520 remains stationary with respect to the object OBJ and does not rotate during the data acquisition.

Both the X-ray source 512, collimator 514 (e.g., a bow-tie filter), and the detector unit 503 rotate around the object OBJ while the photon-counting detectors PCD1 through PCDN are stationary with respect to the object OBJ. In one implementation, the X-ray source 512 projects X-ray radiation with a predetermined source fan beam angle $\theta_A$ towards the object OBJ while the X-ray source 512 rotates around the object OBJ outside the sparsely placed photon-counting detectors PCD1 through PCDN. Furthermore, the detector unit 503 is mounted at a diametrically opposed position from the X-ray source 512 across the object OBJ and rotates outside the stationary circular component 520, on which the photon-counting detectors PCD1 through PCDN are fixed in a predetermined sparse arrangement.

In one implementation, the X-ray source 512 optionally travels a helical path relative to the object OBJ, wherein the table 516 moves the object OBJ linearly in a predetermined direction perpendicular to the rotational plane of the rotating portion 510 as the rotating portion 510 rotates the X-ray source 512 and detector unit 503 in the rotational plane.

The motion of the rotating component 510 around the object OBJ is controlled by a motion control system. The motion control system can be integrated with a data acquisition system or can be separate providing one way information regarding the angular position of the rotating component 510 and the linear position of the table 516. The motion control system can include position encoders and feedback to control the position of the rotating component 510 and the table 516. The motion control system can be an open loop system, a closed loop system, or a combination of an open loop system and a closed loop system. The motion control system can use linear and rotary encoders to provide feedback related to the position of the rotating component 510 and the position of the table 516. The motion control system can use actuators to drive the motion of the rotating component 510 and the motion of the table 516. These positioners and actuators can include: stepper motors, DC motors, worm drives, belt drives, and other actuators known in the art.

The CT scanner also includes a data channel that routes projection measurement results from the photon counting detectors and the detector unit 503 to a data acquisition system 576, a processor 570, memory 578, network controller 574. The data acquisition system 576 controls the acquisition, digitization, and routing of projection data from the detectors. The data acquisition system 576 also includes radiography control circuitry to control the rotation of the annular rotating components 510 and 530. In one implementation data acquisition system 576 will also control the movement of the bed 516, the operation of the X-ray source 512, and the operation of the X-ray detectors 503. The data acquisition system 576 can be a centralized system or alternatively it can be a distributed system. In an implementation, the data acquisition system 576 is integrated with the processor 570. The processor 570 performs functions including reconstructing images from the projection data, pre-reconstruction processing of the projection data, and post-reconstruction processing of the image data.

The pre-reconstruction processing of the projection data can include correcting for detector calibrations, detector nonlinearities, polar effects, noise balancing, and material decomposition. Post-reconstruction processing can include filtering and smoothing the image, volume rendering processing, and image difference processing as needed. The image reconstruction process can be performed using filtered back-projection, iterative image reconstruction methods, or stochastic image reconstruction methods. Both the processor 570 and the data acquisition system 576 can make use of the memory 576 to store, e.g., projection data, reconstructed images, calibration data and parameters, and computer programs.

The processor 570 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art. The memory 578 can be a hard disk drive, CD-ROM drive, DVD drive, FLASH drive, RAM, ROM or any other electronic storage known in the art.

The network controller 574, such as an Intel Ethernet PRO network interface card from Intel Corporation of America, can interface between the various parts of the CT scanner. Additionally, the network controller 574 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the X-ray source 512 is optionally a single energy source. In another implementation, the X-ray source 512 is configured to perform a kV-switching function for emitting X-ray radiation at a predetermined high-level energy and at a predetermined low-level energy. In still another alternative embodiment, the X-ray source 512 is a single source emitting a broad spectrum of X-ray energies. In still another embodiment, the X-ray source 512 includes multiple X-ray emitters with each emitter being spatially and spectrally distinct.

The detector unit 503 can use energy-integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), $BaF_2$, $CaF_2$ (Eu), ZnS(Ag), $CaWO_4$, $CdWO_4$, YAG(Ce), $Y_3Al_5O_{12}$(Ce), GSO, LSO, $LaCl_3$(Ce), $LaBr_3$(Ce), LYSO, BGO, $LaCl_3$ (Ce), $LaBr_3$(Ce), $C_{14}H_{10}$, $C_{14}H_{12}$, and $C_{10}H_8$), an organic liquid (e.g., an organic solvent with a flour such as p-terphenyl ($C_{18}H_{14}$), PBD ($C_{20}H_{14}N_2O$), butyl PBD ($C_{24}H_{22}N_2O$), or PPO ($C_{15}H_{11}NO$)), a plastic (e.g., a flour suspended in a solid polymer matrix), or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

FIG. 6 illustrates an inner ring topology for a CT scanner. The primary difference between the CT scanner in FIG. 5 and the CT scanner in FIG. 6 is that in FIG. 6 the X-ray source 512 and the first rotational component 510 to which the X-ray source 512 is fixed are outside the circular component 520 to which the PCDs are fixed. In one implementation, the back surface of each PCD is provided a protective rear cover to shield the PCDs from irradiation from behind as the X-ray source 512 travels outside the circular component 520 of the sparsely placed photon-counting detectors.

Both the X-ray source 512, collimator 514 (e.g., a bow-tie filter), and the detector unit 503 rotate around the object OBJ in aperture 615 while the photon-counting detectors PCD1 through PCDN are stationary with respect to the object OBJ in aperture 615. In one implementation, the X-ray source 512 and collimator 514 are mounted on the first rotation component 510 mounted in the gantry 540 so that the X-ray source 512 projects X-ray radiation with a predetermined source fan beam angle $\theta_A$ towards the object OBJ while the X-ray source 512 rotates around the object OBJ outside the sparsely placed photon-counting detectors PCD1 through PCDN. Furthermore, the detector unit 503 having energy-integrating detectors arranged in a third-generation geometry is mounted on the second rotation component 530 that is rotatably fixed to the gantry 540. The detector unit 503 is maintained at a position diametrically opposed position from the X-ray source 512 with the object OBJ in the intermediary space between the X-ray source 512 and the detector unit 503—the rotation components 510 and 530 rotating outside the stationary circular component 520, on which the photon-counting detectors PCD1 through PCDN are fixed in a predetermined sparse arrangement.

While certain embodiments have been described, these embodiments have been presented by way of example only, and are not intended to limit the scope of the inventions. Indeed the novel methods and systems described herein may be embodied in a variety of other forms. For instance, the techniques described herein can be applied to reduce computational time required in calibrating a spectral photon-counting detector. Furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A computed-tomography (CT) apparatus, comprising:
a photon-counting detector configured to receive X-rays emitted from an X-ray source; and
a processing circuit configured to
determine, based on a count rate of an incident spectrum and a dead time parameter of the photon-counting detector, a highest pileup order that has a contribution towards an output spectrum of the photon-counting detector that is greater than a threshold corresponding to the pileup order,
calculate, using a detector response model and the incident spectrum, at least one component spectra, wherein each calculated component spectra corresponds to a pileup order that is lower than or equal to the determined highest pileup order; and
sum the at least one calculated component spectra to generate the output spectrum.

2. The CT apparatus of claim 1, wherein the processing circuit is further configured to determine the highest pileup order based on a Poisson distribution having a mean value equal to a product of the count rate and the dead time parameter of the photon-counting detector.

3. The CT apparatus of claim 1, wherein the processing circuit is further configured to set a threshold for each pileup order based on a level of accuracy desired for image reconstruction by the CT apparatus.

4. The CT apparatus of claim 1, wherein the processing circuit is further configured to set the dead time parameter of the photon-counting detector based on the CT apparatus geometry.

5. The CT apparatus of claim 1, wherein the processing circuit is further configured to calculate the at least one component spectra using the detector response model, which includes a time threshold parameter to distinguish between peak pileup events and tail pileup events.

6. A method for determining a response of a stationary photon-counting detector in a computed tomography (CT) scanner, the method comprising:
determining, based on a count rate of an incident spectrum and a dead time parameter of the photon-counting detector, a highest pileup order that has a contribution towards an output spectrum of the photon-counting detector that is greater than a threshold corresponding to the pileup order;
calculating, using a detector response model and the incident spectrum, at least one component spectra, wherein each calculated component spectra corresponds to a pileup order that is lower than or equal to the determined highest pileup order; and
summing the at least one calculated component spectra to generate the output spectrum.

7. The method of claim 6, wherein the determining step comprises determining the highest pileup order based on a Poisson distribution having a mean value equal to a product of the count rate and the dead time parameter of the photon-counting detector.

8. The method of claim 6, further comprising:
setting a threshold for each pileup order based on a level of accuracy desired for image reconstruction by the CT scanner.

9. The method of claim 6, further comprising:
setting the dead time parameter of the photon-counting detector based on the CT scanner geometry.

10. The method of claim 6, wherein the calculating step comprises calculating the at least one component spectra using the detector response model, which includes a time threshold parameter to distinguish between peak pileup events and tail pileup events.

11. A non-transitory computer-readable medium having stored thereon a program that, when executed by a computer, causes the computer to execute a method comprising:
determining, based on a count rate of an incident spectrum and a dead time parameter of a photon-counting detector in a computed tomography (CT) scanner, a highest pileup order that has a contribution towards an output spectrum of the photon-counting detector that is greater than a threshold corresponding to the pileup order;
calculating, using a detector response model and the incident spectrum, at least one component spectra, wherein each calculated component spectra corresponds to a pileup order that is lower than or equal to the determined highest pileup order; and
summing the at least one calculated component spectra to generate the output spectrum.

12. The non-transitory computer readable medium of claim 11, wherein the determining step comprises determining the highest pileup order based on a Poisson distribution having a mean value equal to a product of the count rate and the dead time parameter of the photon-counting detector.

13. The non-transitory computer readable medium of claim 11, wherein the method further comprises:
setting a threshold for each pileup order based on a level of accuracy desired for image reconstruction by the CT scanner.

14. The non-transitory computer readable medium of claim 11, wherein the method further comprises:
setting the dead time parameter of the photon-counting detector based on the CT scanner geometry.

15. The non-transitory computer readable medium of claim 11, wherein the calculating step comprises calculating the at least one component spectra using the detector response model, which includes a time threshold parameter to distinguish between peak pileup events and tail pileup events.

16. The CT apparatus of claim 1, wherein the processing circuit is further configured to perform image reconstruction using the generated output spectrum.

* * * * *